United States Patent [19]

Peyman et al.

[11] Patent Number: 5,563,050
[45] Date of Patent: Oct. 8, 1996

[54] ANTISENSE OLIGONUCLEOTIDES AGAINST HSV 1, AND THEIR PREPARATION

[75] Inventors: Anuschirwan Peyman, Kelkheim; Eugen Uhlmann, Glashütten; Matthias Mag, Oberursel; Gerhard Kretzschmar, Eschborn; Matthias Helsberg, Kelkheim; Irvin Winkler, Liederbach, all of Germany

[73] Assignee: Hoechst Aktiengesellschaft, Frankfurt am Main, Germany

[21] Appl. No.: 281,082

[22] Filed: Jul. 27, 1994

[30] Foreign Application Priority Data

Sep. 17, 1993 [DE] Germany .................... 43 31 670.0

[51] Int. Cl.$^6$ ................... C12P 19/34; C12Q 1/68; A61K 31/70
[52] U.S. Cl. .................. 435/91.1; 435/6; 435/91.33; 435/172.1; 435/172.3; 435/240.2; 536/23.1; 536/24.5; 514/44
[58] Field of Search ................ 435/91.1, 91.33, 435/91.21.172.1, 172.3, 6, 240.2; 514/44; 536/23.1, 24.5

[56] References Cited

U.S. PATENT DOCUMENTS

| | | | |
|---|---|---|---|
| 5,138,045 | 8/1992 | Cook et al. | 536/24.5 |
| 5,248,670 | 9/1993 | Arapes et al. | 514/44 |

FOREIGN PATENT DOCUMENTS

| | | |
|---|---|---|
| 552 766 A2 | 1/1993 | European Pat. Off. |
| WO92/05284 | 4/1992 | WIPO. |

OTHER PUBLICATIONS

Sanbrook et al., Molecular Cloning: A Laboratory Manual, 2nd Ed. CSHL Press, NY 1989, p. 11.4.
McGeoch et al. J. Gen. Vir. 69:1531–1574, 1988.
Stein et al. Science 261:1004–1012 (1993).
Kole et al. Adv. Drug Der. Revs. 6:271 (1991).
McGraw et al. BioTechniques 8:674 (1990).
Eugen Uhlmann et al., "Antisense Oligonucleotides: A New Therapeutic Principle," Chemical Reviews, 90 (4): 544–584 (1990).
John F. Milligan et al., "Current Concepts in Antisense Drug Design," Journal of Medicinal Chemistry, 36(14): 1923–1937 (1993).
Wen-Yi Gao et al., "Mechanisms of Inhibition of Herpes Simplex Virus Type 2 Growth by 28-mer Phosphorothioate Oligodeoxycytidine," Journal of Biological Chemistry, 265(33): 20172–20178 (1990).
M. Kulka et al., "Site Specificity of the Inhibitory Effects of Oligo(nucleoside methylphosphonate)s Complementary to the Acceptor Splice Junction of Herpes Simplex Virus Type 1 Immediate Early mRNA 4," Proc. Nat'l Acad. Sci. USA, 86: 6868–6872 (1989).
P. Dan Cook, "Medicinal Chemistry of Antisense Oligonucleotides— Future Opportunities," Anti–Cancer Drug Design, 6: 585–607 (1991).

John Goodchild, "Conjugates of Oligonucleotides and Modified Oligonucleotides: A Review of Their Synthesis and Properties," Bioconjugate Chemistry, 1(3): 165–187 (1990).
Serge L. Beaucage et al., "The Synthesis of Modified Oligonucleotides by the Phosphoramidite Approach and Their Applications," Tetrahedron Report No. 335, 49(28): 6123–6194 (1993).
F. Eckstein (ed.), "Olgonucleotides and Analogues—A Practical Approach," IRL Press at Oxford University Press, pp. ix–xxi.
Eugene P. Stirchak et al., "Uncharged Stereoregular Nucleic Acid Analogs: 2. Morpholino Nucleoside Obligomers with Carbamate Internucleoside Linkages," Nucleic Acids Research, 17(15): 6129–6141 (1989).
Jeffery C. Hanvey et al., "Antisense and Antigene Properties of Peptide Nucleic Acids," Science, 258: 1481–1485 (1992).
Masakazu Koga et al., "Alternating α,β–Oligothymidylates with Alternating(3'—3')–and (5'—5')–Internucleotidic Phosphodiester Linkages as Models for Antisense Oligodeoxyribonucleotides," The Journal of Organic Chemistry, 56(12): 3757–3759 (1991).
M. Sawadogo et al., "A Rapid Method for the Purification of Deprotected Oligodeoxynucleotides," Nucleic Acids Research, 19(3): 674 (1991).

(List continued on next page.)

*Primary Examiner*—John L. LeGuyader
*Attorney, Agent, or Firm*—Finnegan, Henderson, Farabow, Garrett & Dunner, L.L.P.

[57] ABSTRACT

The invention relates to novel antisense oligonucleotides having the sequences

AO1 (Herp099):

5'-GCGGGGCTCCATGGGGGTCG-3' (SEQ ID NO:1)

AO2 (Herp018):

5'-GCAGGAGGATGCTGAGGAGG-3' (SEQ ID NO:2)

AO3 (Herp002):

5'-GGGGCGGGGCTCCATGGGGG-3' (SEQ ID NO:3)

AO4 (Herp112):

5'-GGCGGGGCTCCATGGGGGTC-3' (SEQ ID NO:4)

AO5 (Herp034):

5'-GGGGCTCCATGGGGGTCGTA-3' (SEQ ID NO:5)

AO6 (Herp024):

5'-AAGAGGTCCATTGGGTGGGG-3' (SEQ ID NO:6)

AO7 (Herp028):

5'-GGCCCTGCTGTTCCGTGGCG-3' (SEQ ID NO: 7)

and their mixtures, homologs or modified forms, against HSV 1.

6 Claims, No Drawings

OTHER PUBLICATIONS

Jeffry S. Mann et al., "Synthesis and Properties of an Oligodeoxynucleotide Modified with a Pyrene Derivative at the 5'-Phosphate," Bioconjugate Chem., 3: 554–558 (1992).

F. Schubert et al., "One–step Labelling of Oligonucleotides with Fluoresceine during Automated Synthesis," Nucleic Acids Research, 18(11): 3427 (1990).

Glenn D. Hoke et al., "Effects of Phosphorothioate Capping on Antisense Oligonucleotide Stability, Hybridization and Antiviral Efficacy Versus Herpes Simplex Virus Infection," Nucleic Acids Research, 19(20): 5743–5748 (1991).

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GCGGGGCTCC ATGGGGGTCG     20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCAGGAGGAT GCTGAGGAGG     20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GGGGCGGGGC TCCATGGGGG     20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GGCGGGGCTC CATGGGGGTC     20

( 2 ) INFORMATION FOR SEQ ID NO:5:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:5:

GGGGCTCCAT GGGGGTCGTA                    20

( 2 ) INFORMATION FOR SEQ ID NO:6:

( i ) SEQUENCE CHARACTERISTICS:
         ( A ) LENGTH: 20 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:6:

AAGAGGTCCA TTGGGTGGGG                    20

( 2 ) INFORMATION FOR SEQ ID NO:7:

( i ) SEQUENCE CHARACTERISTICS:
         ( A ) LENGTH: 20 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:7:

GGCCCTGCTG TTCCGTGGCG                    20

( 2 ) INFORMATION FOR SEQ ID NO:8:

( i ) SEQUENCE CHARACTERISTICS:
         ( A ) LENGTH: 24 base pairs
         ( B ) TYPE: nucleic acid
         ( C ) STRANDEDNESS: single
         ( D ) TOPOLOGY: linear ( i i ) MOLECULE TYPE: DNA (genomic)

( i x ) FEATURE:
         ( A ) NAME/KEY: misc_feature
         ( B ) LOCATION: one-of(2, 4, 21, 23)
         ( D ) OTHER INFORMATION: /note="N =a phosphodiester bond
               replaced by a phosphorothioate bridge."

( x i ) SEQUENCE DESCRIPTION: SEQ ID NO:8:

GNCNGGGGCT CCATGGGGGT NCNG               24

( 2 ) INFORMATION FOR SEQ ID NO:9:

( i ) SEQUENCE CHARACTERISTICS:
         ( A ) LENGTH: 24 base pairs
         ( B ) TYPE: nucleic acid
         ( C ) STRANDEDNESS: single
         ( D ) TOPOLOGY: linear ( i i ) MOLECULE TYPE: DNA (genomic)

( i x ) FEATURE:
         ( A ) NAME/KEY: misc_feature
         ( B ) LOCATION: one-of(2, 4, 21, 23)
         ( D ) OTHER INFORMATION: /note="N =a phosphodiester bond
               replaced by a phosphorothioate bridge."

( x i ) SEQUENCE DESCRIPTION: SEQ ID NO:9:

GNCNAGGAGG ATGCTGAGGA NGNG    24

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: one-of(2, 4, 21, 23)
        ( D ) OTHER INFORMATION: /note="N =a phosphodiester bond
            replaced by a phosphorothioate bridge."

( x i ) SEQUENCE DESCRIPTION: SEQ ID NO:10:

GNGNGGCGGG GCTCCATGGG NGNG    24

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: one-of(2, 4, 21, 23)
        ( D ) OTHER INFORMATION: /note="N =a phosphodiester bond
            replaced by a phosphorothioate bridge."

( x i ) SEQUENCE DESCRIPTION: SEQ ID NO:11:

GNGNCGGGGC TCCATGGGGG NTNC    24

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: one-of(2, 4, 21, 23)
        ( D ) OTHER INFORMATION: /note="N =a phosphodiester bond
            replaced by a phosphorothioate bridge."

( x i ) SEQUENCE DESCRIPTION: SEQ ID NO:12:

GNGNGGCTCC ATGGGGGTCG NTNA    24

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature (B) LOCATION: one-of(2, 4, 21, 23)
(D) OTHER INFORMATION: /note="N =a phosphodiester bond replaced by a phosphorothioate bridge."

(xi) SEQUENCE DESCRIPTION: SEQ ID NO:13:

ANANGAGGTC CATTGGGTGG NGNG                    24

(2) INFORMATION FOR SEQ ID NO:14:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: one-of(2, 4, 21, 23)
      (D) OTHER INFORMATION: /note="N =a phosphodiester bond replaced by a phosphorothioate bridge."

(xi) SEQUENCE DESCRIPTION: SEQ ID NO:14:

GNGNCCCTGC TGTTCCGTGG NCNG                    24

(2) INFORMATION FOR SEQ ID NO:15:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: one-of(2, 4, 21, 23)
      (D) OTHER INFORMATION: /note="N =a phosphodiester bond replaced by a phosphorothioate bridge."

(xi) SEQUENCE DESCRIPTION: SEQ ID NO:15:

GNGNGCGGGG CTCCATGGGG NGNT                    24

(2) INFORMATION FOR SEQ ID NO:16:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: one-of(2, 4, 21, 23)
      (D) OTHER INFORMATION: /note="N=a phosphodiester bond replaced by a phosphorothioate bridge."

(xi) SEQUENCE DESCRIPTION: SEQ ID NO:16:

CNCNGGGGCG GGGCTCCATG NGNG                    24

(2) INFORMATION FOR SEQ ID NO:17:

(i) SEQUENCE CHARACTERISTICS:
      (A) LENGTH: 24 base pairs
      (B) TYPE: nucleic acid
      (C) STRANDEDNESS: single
      (D) TOPOLOGY: linear ( i i ) MOLECULE TYPE: DNA (genomic)

( i x ) FEATURE:
    ( A ) NAME/KEY: misc_feature
    ( B ) LOCATION: one-of(2, 4, 21, 23)
    ( D ) OTHER INFORMATION: /note="N=a phosphodiester bond
        replaced by a phosphorothioate bridge."

( x i ) SEQUENCE DESCRIPTION: SEQ ID NO:17:

CNGNGGGCTC CATGGGGGTC NGNT     24

( 2 ) INFORMATION FOR SEQ ID NO:18:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: one-of(2, 4, 21, 23)
    ( D ) OTHER INFORMATION: /note="N =a phosphodiester bond
        replaced by a phosphorothioate bridge."

( x i ) SEQUENCE DESCRIPTION: SEQ ID NO:18:

GNGNGCTCCA TGGGGGTCGT NANT     24

( 2 ) INFORMATION FOR SEQ ID NO:19:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: one-of(2, 4, 21, 23)
    ( D ) OTHER INFORMATION: /note="N =a phosphodiester bond
        replaced by a phosphorothioate bridge."

( x i ) SEQUENCE DESCRIPTION: SEQ ID NO:19:

GNCNTCCATG GGGGTCGTAT NGNC     24

( 2 ) INFORMATION FOR SEQ ID NO:20:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: one-of(2, 4, 21, 23)
    ( D ) OTHER INFORMATION: /note="N =a phosphodiester bond
        replaced by a phosphorothioate bridge."

( x i ) SEQUENCE DESCRIPTION: SEQ ID NO:20:

CNCNGGAAAA CATCGCGGTT NGNT     24

( 2 ) INFORMATION FOR SEQ ID NO:21:

( i ) SEQUENCE CHARACTERISTICS:
    ( A ) LENGTH: 24 base pairs ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: misc_feature
                ( B ) LOCATION: one-of(2, 4, 21, 23)
                ( D ) OTHER INFORMATION: /note="N =a phosphodiester bond
                        replaced by a phosphorothioate bridge."

( x i ) SEQUENCE DESCRIPTION: SEQ ID NO:21:

CNCNGGGGGC GCTTGGCCGG NGNG                                                                                      2 4

( 2 ) INFORMATION FOR SEQ ID NO:22:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: misc_feature
                ( B ) LOCATION: one-of(2, 4, 21, 23)
                ( D ) OTHER INFORMATION: /note="N =a phosphodiester bond
                        replaced by a phosphorothioate bridge."

( x i ) SEQUENCE DESCRIPTION: SEQ ID NO:22:

CNANGCAGCT TGCGGGGCTT NGNG                                                                                      2 4

( 2 ) INFORMATION FOR SEQ ID NO:23:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: misc_feature
                ( B ) LOCATION: one-of(2, 4, 21, 23)
                ( D ) OTHER INFORMATION: /note="N =a phosphodiester bond
                        replaced by a phosphorothioate bridge."

( x i ) SEQUENCE DESCRIPTION: SEQ ID NO:23:

CNCNCCCAAC AGGTGGGAGA NANG                                                                                      2 4

( 2 ) INFORMATION FOR SEQ ID NO:24:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: misc_feature
                ( B ) LOCATION: one-of(2, 4, 21, 23)
                ( D ) OTHER INFORMATION: /note="N =a phosphodiester bond
                        replaced by a phosphorothioate bridge."

( x i ) SEQUENCE DESCRIPTION: SEQ ID NO:24:

GNGNGGGGTG CCACACTTCG NGNG                                                                                      2 4

( 2 ) INFORMATION FOR SEQ ID NO:25:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: one-of(2, 4, 21, 23)
        ( D ) OTHER INFORMATION: /note="N =a phosphodiester bond
            replaced by a phosphorothioate bridge."

( x i ) SEQUENCE DESCRIPTION: SEQ ID NO:25:

CNCNCACCCG AACCCCTAAA NGNA        24

( 2 ) INFORMATION FOR SEQ ID NO:26:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: one-of(2, 4, 21, 23)
        ( D ) OTHER INFORMATION: /note="N =a phosphodiester bond
            replaced by a phosphorothioate bridge."

( x i ) SEQUENCE DESCRIPTION: SEQ ID NO:26:

GNTNCCGCGT TCATGTCGGC NANA        24

( 2 ) INFORMATION FOR SEQ ID NO:27:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: one-of(2, 4, 21, 23)
        ( D ) OTHER INFORMATION: /note="N =a phosphodiester bond
            replaced by a phosphorothioate bridge."

( x i ) SEQUENCE DESCRIPTION: SEQ ID NO:27:

ANANCAGAGG CAGTCAAACA NGNG        24

( 2 ) INFORMATION FOR SEQ ID NO:28:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: one-of(2, 4, 21, 23)
        ( D ) OTHER INFORMATION: /note="N =a phosphodiester bond
            replaced by a phosphorothioate bridge."

( x i ) SEQUENCE DESCRIPTION: SEQ ID NO:28:

ANTNACGGGA AAGACGATAT NCNG                                                                       24

( 2 ) INFORMATION FOR SEQ ID NO:29:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: one-of(2, 4, 21, 23)
        ( D ) OTHER INFORMATION: /note="N =a phosphodiester bond
              replaced by a phosphorothioate bridge."

( x i ) SEQUENCE DESCRIPTION: SEQ ID NO:29:

GNTNCTTCCT GCCCCATTGC NGNT                                                                       24

( 2 ) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: one-of(2, 4, 21, 23)
        ( D ) OTHER INFORMATION: /note="N =a phosphodiester bond
              replaced by a phosphorothioate bridge."

( x i ) SEQUENCE DESCRIPTION: SEQ ID NO:30:

TNGNCGTCCG CGCGCCCAAG NGNG                                                                       24

( 2 ) INFORMATION FOR SEQ ID NO:31:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: one-of(18, 20, 22)
        ( D ) OTHER INFORMATION: /note="N =a phosphodiester bond
              replaced by a phosphorothioate bridge."

( x i ) SEQUENCE DESCRIPTION: SEQ ID NO:31:

GCGGGGCTCC ATGGGGGNTN CNG                                                                        23

( 2 ) INFORMATION FOR SEQ ID NO:32:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: one-of(2, 4, 6)

(D) OTHER INFORMATION: /note="N =a phosphodiester bond
replaced by a phosphorothioate bridge."

(xi) SEQUENCE DESCRIPTION: SEQ ID NO:32:

GNCNGNGGGC TCCATGGGGG TCG                    23

(2) INFORMATION FOR SEQ ID NO:33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1
        (D) OTHER INFORMATION: /note="N =a 5'[4-(1-pyrenyl)
            butanyl]phosphodiester."

(ix) FEATURE:
        (A) NAME/KEY: misc_feature
        (B) LOCATION: one-of(2, 3, 22, 24)
        (D) OTHER INFORMATION: /note="N =a phosphodiester bond
            replaced by a phosphorothioate bridge."

(xi) SEQUENCE DESCRIPTION: SEQ ID NO:33:

NGNCNGGGGC TCCATGGGGG TNCNG                  25

(2) INFORMATION FOR SEQ ID NO:34:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: one-of(2, 4, 21, 23)
        (D) OTHER INFORMATION: /note="N =a phosphodiester bond
            replaced by a phosphorothioate bridge."

(ix) FEATURE:
        (A) NAME/KEY: misc_feature
        (B) LOCATION: 25
        (D) OTHER INFORMATION: /note="N =3'-n-C-14-H-29
            phosphoric ester."

(xi) SEQUENCE DESCRIPTION: SEQ ID NO:34:

GNCNAGGAGG ATGCTGAGGA NGNGN                  25

(2) INFORMATION FOR SEQ ID NO:35:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: one-of(2, 4, 19, 21, 24)
        (D) OTHER INFORMATION: /note="N =a phosphodiester bond
            replaced by a phosphorothioate bridge."

(ix) FEATURE:
        (A) NAME/KEY: misc_feature (B) LOCATION: 26
                (D) OTHER INFORMATION: /note="N =3'-n-C-12-H-25
                    phosphoric ester."

(xi) SEQUENCE DESCRIPTION: SEQ ID NO:35:

GNCNAGGAGG ATGCTGAGGN ANGNGN                                            26

(2) INFORMATION FOR SEQ ID NO:36:

(i) SEQUENCE CHARACTERISTICS:
                (A) LENGTH: 26 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: misc_feature
                (B) LOCATION: one-of(2, 4, 19, 21, 23)
                (D) OTHER INFORMATION: /note="N =a phosphodiester bond
                    replaced by a phosphorothioate bridge."

(ix) FEATURE:
                (A) NAME/KEY: misc_feature
                (B) LOCATION: 26
                (D) OTHER INFORMATION: /note="N =a 3'-n-C-14-H-29
                    phosphoric ester."

(xi) SEQUENCE DESCRIPTION: SEQ ID NO:36:

GNCNAGGAGG ATGCTGAGGN ANGNGN                                            26

(2) INFORMATION FOR SEQ ID NO:37:

(i) SEQUENCE CHARACTERISTICS:
                (A) LENGTH: 26 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: misc_feature
                (B) LOCATION: one-of(2, 4, 19, 21, 23)
                (D) OTHER INFORMATION: /note="N =a phosphodiester bond
                    replaced by a phosphorothioate bridge."

(ix) FEATURE:
                (A) NAME/KEY: misc_feature
                (B) LOCATION: 26
                (D) OTHER INFORMATION: /note="N =is a 3'n-C-16-H-33
                    phosphoric ester."

(xi) SEQUENCE DESCRIPTION: SEQ ID NO:37:

GNCNAGGAGG ATGCTGAGGN ANGNGN                                            26

(2) INFORMATION FOR SEQ ID NO:38:

(i) SEQUENCE CHARACTERISTICS:
                (A) LENGTH: 26 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: misc_feature
                (B) LOCATION: one-of(2, 4, 19, 21, 23)
                (D) OTHER INFORMATION: /note="N=is a phosphodiester bond
                    replaced by a phosphorothioate bridge."

(ix) FEATURE:

(A) NAME/KEY: misc_feature
                (B) LOCATION: 26
                (D) OTHER INFORMATION: /note="N =is 3'-n-C-18-H-37
                    phosphoric ester."

(xi) SEQUENCE DESCRIPTION: SEQ ID NO:38:

GNCNAGGAGG ATGCTGAGGN ANGNGN                    26

(2) INFORMATION FOR SEQ ID NO:39:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: misc_feature
                (B) LOCATION: one-of(19, 21)
                (D) OTHER INFORMATION: /note="N =a phosphodiester bond
                    replaced by a phosphorothioate bridge."

(ix) FEATURE:
                (A) NAME/KEY: misc_feature
                (B) LOCATION: 1
                (D) OTHER INFORMATION: /note="N =a
                    3'-hydroxy- 2-(N-thiourea-fluorescein-4-animobutyl
                    ) propyl-1-0-phosphoric ester."

(xi) SEQUENCE DESCRIPTION: SEQ ID NO:39:

NGCGGGGCTC CATGGGGGTN CNG                    23

(2) INFORMATION FOR SEQ ID NO:40:

(i) SEQUENCE CHARACTERISTICS:
                (A) LENGTH: 25 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: misc_feature
                (B) LOCATION: one-of(2, 4, 21, 23)
                (D) OTHER INFORMATION: /note="N =a phosphodiester bond
                    replaced by a phosphorothioate bridge."

(ix) FEATURE:
                (A) NAME/KEY: misc_feature
                (B) LOCATION: 25
                (D) OTHER INFORMATION: /note="N =a 3'phosphate."

(xi) SEQUENCE DESCRIPTION: SEQ ID NO:40:

GNCNGGGGCT CCATGGGGGT NCNGN                    25

(2) INFORMATION FOR SEQ ID NO:41:

(i) SEQUENCE CHARACTERISTICS:
                (A) LENGTH: 25 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: misc_feature
                (B) LOCATION: one-of(2, 4, 21, 23)
                (D) OTHER INFORMATION: /note="N =a phosphodiester bond
                    replaced by a phosphoriothioate bridge."

( i x ) FEATURE:
   ( A ) NAME/KEY: misc_feature
   ( B ) LOCATION: 25
   ( D ) OTHER INFORMATION: /note="N =a
     ?????????????????( c o l l e e n h e l p )."

( x i ) SEQUENCE DESCRIPTION: SEQ ID NO:41:

GNCNGGGGCT CCATGGGGGT NCNGN                 25

( 2 ) INFORMATION FOR SEQ ID NO:42:

( i ) SEQUENCE CHARACTERISTICS:
   ( A ) LENGTH: 25 base pairs
   ( B ) TYPE: nucleic acid
   ( C ) STRANDEDNESS: single
   ( D ) TOPOLOGY: linear ( i i ) MOLECULE TYPE: DNA (genomic)

( i x ) FEATURE:
   ( A ) NAME/KEY: misc_feature
   ( B ) LOCATION: 2
   ( D ) OTHER INFORMATION: /note="N =a
     3'-hydroxy- 2-(N-thiourea-fluorescein-4-aminobutyl)
     propyl-1-0- phosphoric ester."

( i x ) FEATURE:
   ( A ) NAME/KEY: misc_feature
   ( B ) LOCATION: one-of(21, 23)
   ( D ) OTHER INFORMATION: /note="N =a phosphodiester bond
     replaced by a phosphorothioate bridge."

( i x ) FEATURE:
   ( A ) NAME/KEY: misc_feature
   ( B ) LOCATION: 25
   ( D ) OTHER INFORMATION: /note="N =a 3'vitamin E
     phosphoric ester."

( x i ) SEQUENCE DESCRIPTION: SEQ ID NO:42:

GNGCGGGGCT CCATGGGGGT NCNGN                 25

( 2 ) INFORMATION FOR SEQ ID NO:43:

( i ) SEQUENCE CHARACTERISTICS:
   ( A ) LENGTH: 25 base pairs
   ( B ) TYPE: nucleic acid
   ( C ) STRANDEDNESS: single
   ( D ) TOPOLOGY: linear ( i i ) MOLECULE TYPE: DNA (genomic)

( i x ) FEATURE:
   ( A ) NAME/KEY: misc_feature
   ( B ) LOCATION: one-of(2, 4, 6, 22, 24)
   ( D ) OTHER INFORMATION: /note="N =a phosphodiester bond
     replaced by a phosphorothioate bridge."

( x i ) SEQUENCE DESCRIPTION: SEQ ID NO:43:

GNGNCNGGGG CTCCATGGGG GNTNC                 25

( 2 ) INFORMATION FOR SEQ ID NO:44:

( i ) SEQUENCE CHARACTERISTICS:
   ( A ) LENGTH: 26 base pairs
   ( B ) TYPE: nucleic acid
   ( C ) STRANDEDNESS: single
   ( D ) TOPOLOGY: linear ( i i ) MOLECULE TYPE: DNA (genomic)

( i x ) FEATURE:
   ( A ) NAME/KEY: misc_feature
   ( B ) LOCATION: one-of(2, 4, 6, 22, 24)
   ( D ) OTHER INFORMATION: /note="N =a phosphodiester bond replaced by a phosphorothioate bridge."

( i x ) FEATURE:
    ( A ) NAME/KEY: misc_feature
    ( B ) LOCATION: 26
    ( D ) OTHER INFORMATION: /note="N =a 3'-n-C-14-H-29
        phosphoric ester."

( x i ) SEQUENCE DESCRIPTION: SEQ ID NO:44:

GNGNCNGGGG CTCCATGGGG GNTNCN      26

( 2 ) INFORMATION FOR SEQ ID NO:45:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: one-of(2, 4, 6, 22, 24)
        ( D ) OTHER INFORMATION: /note="N =a phosphodiester bond
            replaced by a phosphorothioate bridge."

( i x ) FEATURE:
        ( A ) NAME/KEY: misc_feature
        ( B ) LOCATION: 26
        ( D ) OTHER INFORMATION: /note="N =a 3'-batyl phosphoric
            ester."

( x i ) SEQUENCE DESCRIPTION: SEQ ID NO:45:

GNGNCNGGGG CTCCATGGGG GNTNCN      26

( 2 ) INFORMATION FOR SEQ ID NO:46:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: one-of(2, 4, 22, 24)
        ( D ) OTHER INFORMATION: /note="N =a phosphodiester bond
            replaced by a phosphorothioate bridge."

( x i ) SEQUENCE DESCRIPTION: SEQ ID NO:46:

CNCNAGGGTA CAGGTGGCCG GNCNC      25

( 2 ) INFORMATION FOR SEQ ID NO:47:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: one-of(2, 4, 22, 24)
        ( D ) OTHER INFORMATION: /note="N =a phosphodiester bond
            replaced by a phosphorothioate bridge."

( i x ) FEATURE:
        ( A ) NAME/KEY: misc_feature
        ( B ) LOCATION: 26

(D) OTHER INFORMATION: /note="N =a 3'-n-C-14-H29 phosphoric ester."

(xi) SEQUENCE DESCRIPTION: SEQ ID NO:47:

CNCNAGGGTA CAGGTGGCCG GNCNCN    26

(2) INFORMATION FOR SEQ ID NO:48:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: one-of(2, 4, 21, 23, 25)
        (D) OTHER INFORMATION: /note="N =a phosphodiester bond replaced by a phosphorothioate bridge."

(ix) FEATURE:
        (A) NAME/KEY: misc_feature
        (B) LOCATION: 27
        (D) OTHER INFORMATION: /note="N =a 3'-n-C-12-H25 phosphoric ester."

(xi) SEQUENCE DESCRIPTION: SEQ ID NO:48:

CNCNAGGGTA CAGGTGGCCG NGNCNCN    27

(2) INFORMATION FOR SEQ ID NO:49:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: one-of(2, 4, 22, 24)
        (D) OTHER INFORMATION: /note="N =a phosphodiester bond replaced by a phosphorothioate bridge."

(ix) FEATURE:
        (A) NAME/KEY: misc_feature
        (B) LOCATION: 26
        (D) OTHER INFORMATION: /note="N =a 3'-n-C-14-H29 phosphoric ester."

(xi) SEQUENCE DESCRIPTION: SEQ ID NO:49:

CNCNAGGGTA CAGGTGGCCG GNCNCN    26

(2) INFORMATION FOR SEQ ID NO:50:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

GCATACGACC CCCATGGAGC CCCGCCCCGG    30

(2) INFORMATION FOR SEQ ID NO:51:

(i) SEQUENCE CHARACTERISTICS:

(A) LENGTH: 24 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: one-of(2, 4, 21, 23)
(D) OTHER INFORMATION: /note="N =a phosphodiester bond replaced by a phosphorothioate bridge."

(xi) SEQUENCE DESCRIPTION: SEQ ID NO:51:

GNCNGGGGCT CCATGGGGGT NCNG  24

ANTISENSE OLIGONUCLEOTIDES AGAINST HSV 1, AND THEIR PREPARATION

Human herpesviruses are characterized by a series of common features, for example common structural morphology, certain aspects of replication, and the ability to cause life-long infections. This applies particularly to type 1 and type 2 herpes simplex viruses (HSV 1 and HSV 2). HSV causes a broad spectrum of diseases which extend from relatively mild lesions of the skin, of the mucous membrane and of the corneal epithelium right through to serious cases of encephalitis which often have a fatal outcome. Periodic reactivations of the latent virus during the lifetime of the host result in recurring skin lesions, often accompanied by a significant degree of morbidity.

There are a variety of approaches to antiviral therapy in the case of HSV. Thus, antisense oligonucleotides, for example, selectively inhibit vital gene expression and therefore have the potential to protect cells at the molecular level from latency or from reactivation.

Antisense oligonucleotides are complementary to a specific messenger RNA sequence, bind specifically to this sequence and in this way specifically inhibit gene expression [E. Uhlmann and A. Peyman, Chemo Rev. 90 (1990) 543].

In addition to the known requirements for antisense oligonucleotides, such as, for example, stability towards nucleases, ability to gain access to the cell, etc., the choice of the target sequence on which the antisense oligonucleotides are to exert their effect is of great importance. Although many regions of the RNA are usually suitable for hybridization, there are certain regions which bring about a particularly strong inhibition of gene expression. The requirements with regard to stability towards nucleases, ability to gain access to the cell, etc., can be met by chemical modifications, for example by modifying the phosphate bridge, varying the sugar building block, etc. The choice of the target sequence is determined solely by the sequence of the bases, while other structural elements, such as, for example, the sugar-phosphate backbone can be modified, provided that the ability to hybridize is not restricted by the modification (for example, phosphorothioates instead of phosphoric diesters). Modified bases can also be employed provided that the specificity of the Watson-Crick base pairing is not altered by the modification (for example 5-methylcytosine in place of cytosine).

Reports have been presented on the use, for controlling the virus, of antisense oligonucleotides which are complementary to certain regions of the HSV 1 genome.

In summary, it can be said that "all" phosphorothioates, i.e. oligonucleotides in which the phosphoric diester bridges are all replaced by phosphorothioate bridges, are inhibitors of HSV 1 in cell culture (in this context, see, for example, J. F. Milligan et al., J. Med. Chem. 36 (1993) 1923). A 21mer phosphorothioate antisense oligonucleotide against UL 13 mRNA inhibits the virus by more than 90% at a concentration of 4 µM (G. D. Hoke et al., Nucleic Acids Res 19 (1991) 5743). The same sequence is not active when it is employed as an unmodified oligonucleotide or as an oligonucleotide carrying in each case three phosphorothioate bridges at the 5' or 3' end. At the same time, "all" phosphorothioate oligonucleotides exhibit substantial non-specific effects which are attributable to other mechanisms than the antisense mechanism. Thus, $S(dC)_{28}$, for example, inhibits HSV 1 by 90% even at a concentration of 1 µM (W. Gao et al., J. Biol. Chem. 265 (1990) 20172). Methylphosphonate oligonucleotides are another class of compound which have been tested against HSV 1. A series of four 12 mer antisense oligonucleotides, which were directed against overlapping sequences of the exon/intron region of the 5' splice acceptor site of the IE 4 gene of HSV 1, were tested individually at 100 µM and produced only widely scattered virus inhibition results of from 9 to 98%. A 12 mer antisense oligonucleotide against the translation start of IE110 likewise exhibited either only minimal inhibition, or else no inhibition at all, of HSV 1 (M. Kulka et al., Proc. Natl. Acad. Sci. U.S.A. 86 (1989) 6868, L. Aurelian et al. WO 92/05284 [PCT/US91/06646]).

Surprisingly, we have found that it is in no case sufficient to direct an antisense oligonucleotide against one, even limited, segment of the sequence of a target gene, but that, instead, minimal displacements along the target sequence can lead to large variations in activity. For example, it is not sufficient to use an antisense oligonucleotide which is complementary to the translation start of the IE110 gene of HSV 1, but, instead, only some few of the large number of conceivable sequences prove to be active against HSV 1, as is made clear in Table 1. Under the test conditions employed (tests only using concentrations of less than 80 µM of oligonucleotide), other sequences in turn either exhibit no activity or only a minimal activity. We were able to obtain comparable results for other target genes (Tables 2–4). Surprisingly, we were able to identify antisense oligonucleotides which exhibit a good level of activity against HSV 1 although they only possess those minimal chemical modifications (two phosphorothioate bridges in each case at either the 5' or 3' end) which did not exhibit any activity against HSV 1 in the "best" sequences which have previously been described (G. D. Hoke et al., Nucleic Acids Res 19 (1991) 5743).

The present invention therefore relates to antisense oligonucleotides having the sequence:

AO1 (Herp099):

5'-GCGGGGCTCCATGGGGGTCG-3' (SEQ ID NO:1)

AO2 (Herp018):

5'-GCAGGAGGATGCTGAGGAGG-3' (SEQ ID NO:2)

AO3 (Herp002):

5'-GGGGCGGGGCTCCATGGGGG-3' (SEQ ID NO:3)

AO4 (Herp112):

5'-GGCGGGGCTCCATGGGGGTC-3' (SEQ ID NO:4)

AO5 (Herp034):

5'-GGGGCTCCATGGGGGTCGTA-3' (SEQ ID NO:5)

AO6 (Herp024):

5'-AAGAGGTCCATTGGGTGGGG-3' (SEQ ID NO:6)

or

AO7 (Herp028):

5'-GGCCCTGCTGTTCCGTGGCG-3' (SEQ ID NO: 7)

and mixtures thereof.

The preferred sequences are:

AO1 (Herp099): 5'-G C G G G G C T C C A T G G G G G T C G-3' (SEQ ID NO: 1)

AO2 (Herp018): 5'-G C A G G A G G A T G C T G A G G A G G-3' (SEQ ID NO: 2)

AO3 (Herp002): 5'-G G G C G G G G C T C C A T G G G G G-3' (SEQ ID NO: 3)

The sequence which is particularly preferred is:

AO1 (Herp099): 5'-G C G G G G C T C C A T G G G G G T C G-3' (SEQ ID NO: 1)

The invention also relates to oligonucleotides according to the invention which are truncated or extended at the respective ends, independently of each other, by up to two nucleotides, preferably up to one nucleotide. In addition, the invention relates to their 90%, especially their 95%, homologs and modified antisense oligonucleotides.

In this context, modified antisense oligonucleotides are understood to mean chemical modifications which improve the properties of antisense oligonucleotides, such as, for example, stability towards nucleases and ability to gain access to the cell, and which are known to the person skilled in the art (for example: E. Uhlmann and A. Pepan, Chem. Rev. 90 (1990) 543; P. D. Cook, Anti-Cancer Drug Design 6 (1991) 585; J. Goodchild, Bioconjugate Chem. 1 (1990) 165; S. L. Beaucage and R. P. Iyer, Tetrahedron 49 (1993) 6123; F. Eckstein, Ed., "Oligonucleotides and Analogues—A Practical Approach", IRL Press 1991).

Examples of such modifications are:

a) Modifications of the phosphate bridge; those which may be mentioned by way of example are phosphorothioates, phosphorodithioates, methylphosphonates, phosphoramidates, boranophosphates, phosphate methyl esters, phosphate ethyl esters and phenylphosphonates. Those modifications of the phosphate bridge which are preferred are phosphorothioates and methylphosphonates. The replacement of all of the phosphate bridges of the oligonucleotides according to the invention by the said modifications is to be excepted.

b) Replacement of the phosphate bridges those which may be mentioned by way of example are replacement by formacetal, 3'-thioformacetal, methylhydroxylamine, oxime, methylenedimethylhydrazo, dimethylenesulfone and silyl groups. Replacement by formacetals and 3'-thioformacetals is preferred.

c) Modifications of the sugars those which may be mentioned by way of example are α-anomeric sugars, 2'-O-methylribose, 2'-O-butylribose, 2'-O-allylribose, 2'-fluoro-2'-deoxyribose, 2'-amino-2'-deoxyribose, α-arabinofuranose and carbocyclic sugar analogs. The preferred modification is that with 2'-O-methylribose.

d) Modifications of the bases which do not diminish the specificity of the Watson-Crick base pairings those which may be mentioned by way of example are 5-propyne-2'-deoxyuridine, 5-propyne-2'-deoxycytidine, 5-fluoro-2'-deoxycytidine, 5-fluoro-2'-deoxyuridine, 5-hydroxymethyl-2'-deoxyuridine, 5-methyl-2'-deoxycytidine and 5-bromo-2'-deoxycytidine. The preferred modifications are 5-propyne-2'-deoxyuridine and 5-propyne-2'-deoxycytidine.

e) Replacement of the sugar phosphate backbone, for example with "morpholinonucleoside" oligomers [E. P.

Stirchak et al., Nucleic Acids Res. 17 (1989) 6129] or with "peptide nucleic acids" [e.g. Hanvey et al., Science 258 (1992) 1481].

f) 5' and 3' phosphates and also 5' and 3' thiophosphates.

g) Conjugates, for example at the 3' or at the 5' end (see EP-A2-0 552 766 as well for the 3' derivatization); those which may be mentioned by way of example are conjugates with DMAB-3' or polylysine, with intercalating agents, such as pyrene, acridine, phenazine or phenanthridine, with fluorescent compounds, such as fluorescein, with cross linkers, such as psoralene or azidoproflavine, with lipophilic molecules, such as $C_{12}$–$C_{20}$-alkyl, with lipids, such as 1,2-dihexadecyl-rac-glycerol, with steroids, such as cholesterol or testosterone, with vitamins, such as vitamin E, with polyethylene glycol or oligoethylene glycol, with ($C_1$–$C_{18}$)-alkyl phosphate diesters, with —O—$CH_2$—CH(OH)—O—($C_{12}$–$C_{18}$)-alkyl, in particular conjugates with pyrene derivatives, such as, for example, the compound A026 according to the invention.

h) 3'-3' and 5'-5' inversions (e.g. M. Koga et al., J. Org. Chem. 56 (1991) 3757].

The following modifications are particularly preferred:

a) Replacement of the phosphate bridges by phosphorothioares, phosphorodithioates or methylphosphonates. Replacement of all the phosphate bridges of the oligonucleotides according to the invention by the said modifications is to be excepted.

b) Conjugates with lipophilic molecules, such as $C_{12}$–$C_{20}$-alkyl, with steroids, such as cholesterol or testosterone, with polyethylene glycol or oligoethylene glycol, with vitamin E, with intercalating agents, such as pyrene, with ($C_{14}$–$C_{18}$)-alkyl phosphate diesters and with O—$CH_2$—CH(OH)—O—($C_{12}$–$C_{16}$)-alkyl.

The following modifications are especially preferred:

a) The replacement of one, two or three phosphate bridges at the 5' and/or 3' end by phosphorothioates, in particular the replacement of two phosphate bridges at the 5' and 3' ends by phosphorothioate or phosphorodithioate.

b) The replacement of one, two or three phosphate bridges at the 5' and/or 3' ends by phosphorothioares and, in addition to this, the replacement of 1–5 phosphate bridges by phosphorothioates in the middle.

c) Conjugates with polyethylene glycol, hexaethylene glycol, cholesterol, testosterone, pyrene, batyl and vitamin E, with ($C_{14}$–$C_{18}$)-alkyl phosphate diesters and with —O—$CH_2$—CH(OH)—O—($C_{12}$–$C_{16}$)-alkyl, in particular in combination with the replacement of one, two or three phosphate bridges at the 5' and/or 3' ends with phosphorothioates.

The invention furthermore relates to processes for preparing the compounds according to the invention by methods known to the person skilled in the art, in particular chemical synthesis, to the use of the compounds according to the invention for preparing a pharmaceutical against HSV 1, to a process for preparing a pharmaceutical against HSV 1, wherein one or more of the compounds according to the invention is/are mixed with a physiologically acceptable excipient as well as, where appropriate, suitable additives and/or auxiliary substances, and also to the use of the compounds according to the invention for preparing a pharmaceutical against HSV 1.

Injection represents a preferred form of administration. For this purpose, the antisense oligonucleotides are formulated in a liquid solution, preferably in a physiologically acceptable buffer such as, for example, Hank's solution or Ringer's solution. However, the antisense oligonucleotides may also be formulated in solid form and dissolved or suspended prior to use. The dosages which are preferred for systemic administration are from about 0.01 mg/kg to about 50 mg/kg of body weight and per day.

The following examples are intended to explain the invention in more detail.

EXAMPLE 1

Oligonucleotide synthesis

Unmodified oligonucleotides were synthesized on an automatic DNA synthesizer (Applied Biosystems Model 380B or 394) using the standard phosphoramidite chemistry and oxidation with iodine. In order to introduce phosphorothioate bridges in mixed phosphorothioates and phosphodiester oligonucleotides, oxidation took place using TETD (tetraethylthiuramdisulfide) instead of iodine (Applied Biosystems User Bulletin 65). Following cleavage from the solid support (CPG or Tentagel) and removal of the protective groups using conc. $NH_3$ at 55° C. for 18 h, the oligonucleotides were initially purified by butanol precipitation (Sawadogo, Van Dyke, Nucl. Acids Res. 19 (1991) 674). The sodium salt was then obtained by precipitation from an 0.5M solution of NaCl using 2.5 parts by volume of ethanol.

The [4-(1-pyrenyl)butanyl]phosphodiester is introduced at the 5' end as described in J. S. Mann et al., Bioconj. Chem. 3 (1992) 554.

The oligonucleotides were analyzed by a) Analytical gel electrophoresis in 20% acrylamide, 8M urea, 45 mM Tris-borate buffer, pH 7.0 and/or b) HPLC analysis: Water's GenPak FAX, gradient $CH_3CN$ (400 ml), $H_2O$ (1.61), $NaH_2PO_4$ (3.1 g), NaCl (11.7 g), pH 6.8 (0.1M in NaCl) after $CH_3CN$ (400 ml), $H_2O$ (1.61), $NaH_2PO_4$ (3.1 g), NaCl (175.3 g), pH 6.8 (1.5M in NaCl) and/or c) Capillary gel electrophoresis, Beckmann Kapillare eCAP®, U100P gel column, length, 65 cm, I.D., 100 mm, window 15 cm from one end, buffer, 140 μM Tris, 360 μM boric acid, 7M urea.

and/or d) Electrospray mass spectroscopy.

The analysis of the oligonucleotides showed that they were in each case present in a purity of greater than 90%.

The following oligonucleotides were synthesized:

| No | Sequence[a] | Target[b] | |
|---|---|---|---|
| AO1 (Herp099): | 5'-G*C*G G G G C T C C A T G G G G G T*C*G-3' | IE110, TI | (SEQ ID NO: 8) |
| AO2 (Herp018): | 5'-G*C*A G G A G G A T G C T G A G G A*G*G-3' | UL30, DNA-Pol, Middle | (SEQ ID NO: 9) |
| AO3 (Herp002): | 5'-G*G*G G C G G G G C T C C A T G G *G*G-3' | IE110, TI | (SEQ ID NO: 10) |
| AO4 (Herp112): | 5'-G*G*C G G G G C T C C A T G G G G *T*C-3' | IE110, TI | (SEQ ID NO: 11) |
| AO5 (Herp034): | 5'-G*G*G G C T C C A T G G G G G T C G*T*A-3' | IE110, TI | (SEQ ID NO: 12) |
| AO6 (Herp024): | 5'-A*A*G A G G T C C A T T G G G T G G*G*G-3' | UL48, α-TIF, TI | (SEQ ID NO: 13) |
| AO7 (Herp028): | 5'-G*G*C C C T G C T G T T C C G T G G*C*G-3' | UL52, Middle | (SEQ ID NO: 14) |
| AO8 (HERP111): | 5'-G*G*G C G G G G C T C C a T G G G G*G*T-3' | IE110, TI | (SEQ ID NO: 15) |
| AO9 (HERP100): | 5'-C*C*G G G G C G G G G C T C C A T G*G*G-3' | IE110, TI | (SEQ ID NO: 16) |
| AO10(HERP113): | 5'-C*G*G G G C T C C a T G G G G G T C*G*T-3' | IE110, TI | (SEQ ID NO: 17) |
| AO11(HERP114): | 5'-G*G*G C T C C A T G G G G G T C G T*A*T-3' | IE110, TI | (SEQ ID NO: 18) |
| AO12(HERP115): | 5'-G*C*T C C A T G G G G G T C G T A T*G*C-3' | IE110, TI | (SEQ ID NO: 19) |
| AO13(HERP017): | 5'-C*C*G G A A A A C A T C G C G G T T*G*T-3' | UL30, DNA-POL., TI | (SEQ ID NO: 20) |
| AO14(HERP091): | 5'-C*C*G G G G G C G C T T G G C C G G*G*G-3' | UL30, DNA-POL., Middle | (SEQ ID NO: 21) |
| AO15(HERP092): | 5'-C*A*G C A G C T T G C G G G G C T T*G*G-3' | UL30, DNA-POL., Middle | (SEQ ID NO: 22) |
| AO16(HERP093): | 5'-C*C*C C C A A C A G G T G G G A G A*A*G-3' | UL30, DNA-POL., Middle | (SEQ ID NO: 23) |
| AO17(HERP094): | 5'-G*G*G G G G T G C C A C A C T T C G*G*G-3' | UL30, DNA-POL., Middle | (SEQ ID NO: 24) |
| AO18(HERP016): | 5'-C*C*C A C C C G A A C C C C T A A A*G*A-3' | UL30, 5'-untranslated | (SEQ ID NO: 25) |
| AO19(HERP023): | 5'-G*T*C C G C G T T C A T G T C G G C*A*A-3' | UL48, α-TIF, TI | (SEQ ID NO: 26) |
| AO20(HERP022): | 5'-A*A*C A G A G G C A G T C A A A C A*G*G-3' | UL48, α-TIF, Middle | (SEQ ID |

-continued

| No | Sequence[a] | Target[b] | |
|---|---|---|---|
| AO21(HERP025): | 5'-A*T*A C G G G A A A G A C G A T A T*C*G-3' | UL48, 5'-untranslated | (SEQ ID NO: 27) |
| AO22(Herp027): | 5'-G*T*C T T C C T G C C C C A T T G C*G*T-3' | UL52, TI | (SEQ ID NO: 28) |
| AO23(HERP026): | 5'-T*G*C G T C C G C G C G C C C A A G*G*G-3' | UL52, 5'-untranslated | (SEQ ID NO: 29) |
| AO24: | 5'-G C G G G G C T C C A T G G G G G*T*C*G-3' | IE110, TI | (SEQ ID NO: 30) |
| AO25: | 5'-G*C*G*G G G C T C C A T G G G G G T C G-3' | IE110, TI | (SEQ ID NO: 31) |
| AO26: | 5'-PY-G*C*G G G G C T C C A T G G G G G T*C*G-3' | IE110, TI | (SEQ ID NO: 32) |
| AO27: | 5'-G*C*A G G A G G A T G C T G A G G A*G*G-P-C$_{14}$-3' | UL30, DNA-POL., Middle | (SEQ ID NO: 33) |
| AO28: | 5'-G*C*A G G A G G A T G C T G A G G*A*G*G-P-C$_{12}$-3' | UL30, DNA-POL., Middle | (SEQ ID NO: 34) |
| AO29: | 5'-G*C*A G G A G G A T G C T G A G G*A*G*G-P-C$_{14}$-3' | UL30, DNA-POL., Middle | (SEQ ID NO: 35) |
| AO30: | 5'-G*C*A G G A G G A T G C T G A G G*A*G*G-P-C$_{16}$-3' | UL30, DNA-POL., Middle | (SEQ ID NO: 36) |
| AO31: | 5'-G*C*A G G A G G A T G C T G A G G*A*G*G-P-C$_{18}$-3' | UL30, DNA-POL., Middle | (SEQ ID NO: 37) |
| AO38: | 5'-FAM-G C G G G G C T C C A T G G G G G T*C*G-3' | JE110, TI | (SEQ ID NO: 38) |
| AO39: | 5'-G*C*G G G G C T C C A T G G G G G T*C*G-P-3' | JE110, TI | (SEQ ID NO. 39) |
| AO40: | 5'-G*C*G G G G C T C C A T G G G G G T*C*G-P-DMAB-3' | JE110, TI | (SEQ ID NO: 40) |
| AO41: | 5'-G-FAM-G C G G G G C T C C A T G G G G G T*C*G-P-VITE-3' | JE110, TI | (SEQ ID NO: 41) |
| AO42: | 5'-G*G*C*G G G G C T C C A T G G G G G*T*C-3' | JE110, TI | (SEQ ID NO: 42) |
| AO43: | 5'-G*G*C*G G G G C T C C A T G G G G G*T*C-P-C$_{14}$-3' | JE110, TI | (SEQ ID NO: 43) |
| AO44: | 5'-G*G*C*G G G G C T C C A T G G G G G*T*C-P-BAT-3' | JE110, TI | (SEQ ID NO: 44) |
| Controls: | | | (SEQ ID NO: 45) |
| AO32: | 5'-C*C*A G G G T A C A G G T G G C C G G*C*C-3' | | (SEQ ID NO: 46) |
| AO33: | 5'-C*C*A G G G T A C A G G T G G C C G G*C*C-p-C$_{14}$-3' | | (SEQ ID NO: 47) |
| AO34: | 5'-C*C*A G G G T A C A G G T G G C C G G*C*C-p-C$_{12}$-3' | | (SEQ ID NO: 48) |
| AO35: | 5'-C*C*A G G G T A C A G G T G G C C G G*C*C-p-C$_{14}$-3' | | (SEQ ID NO: 47) | a) The phosphodiester bonds replaced by a phosphorothioate bridge were indicated in the sequence by *; 5'-PY denotes a 5'-[4-(1-pyrenyl)butanyl]phosphodiester;

b) Target sequence on the genome of HSV 1: TI: translation initiation site of the target gene, middle: middle of the target gene.

c) The 3'-derivatized oligonucleotides were synthesized as described in EP 0552766 A2. In this context, p-C$_{12}$-3' is a 3'-n-C$_{12}$H$_{25}$ phosphoric ester, p-C$_{14}$ is a 3'-n-C$_{14}$H$_{29}$ phosphoric ester, p-C$_{16}$ is a 3'-n-C$_{16}$H$_{33}$ phosphoric ester and p-C$_{18}$ is a 3'-n-C$_{18}$H$_{37}$ phosphoric ester; P-3' is a 3' phosphate; P-VITE is a 3' vitamin E phosphoric ester, P-BAT-3'- is a 3'-batyl phosphoric ester; DMAB-3' is

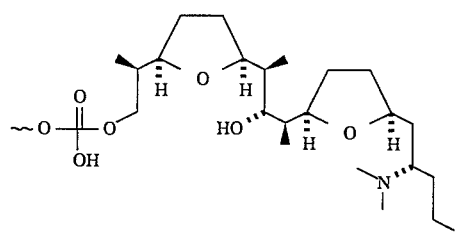

and was introduced by way of a derivatized support (DEr: dimethoxytrityl, CPG: controlled pore glass)

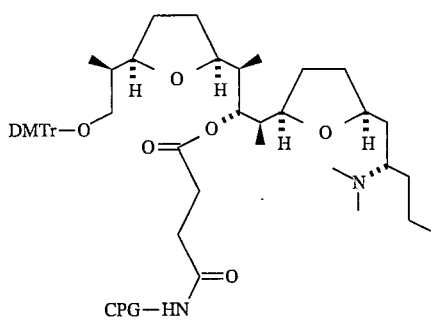

using standard phosphoramidite chemistry.

5'-FAM is 3'-hydroxy-2-(N-thiourea-fluorescein-4-aminobutyl)propyl-1-O-phosphoric ester, which is introduced by way of the corresponding phosphoramidite as in F. Schubert et al., Nucl. Acids Res. 18 (1990) 3427.

EXAMPLE 2

Investigation of the in-vitro antiviral activity of test substances against herpesviruses The antiviral activity of the test substances against different herpesviruses which are pathogenic to humans is investigated in a cell-culture test system.

For the experiment, monkey kidney cells (Vero, $2 \times 10^5$ s/ml) in serum-containing Dulbecco's MEM (5% fetal calf serum, FCS) are sown in 96-well microtiter plates and incubated at 37° C. and at 5% $CO_2$ for 24 h. The serum-containing medium is then sucked off and the cells are rinsed twice with serum-free Dulbecco's MEM (-FCS).

The test substances are prediluted in $H_2O$ to a concentration of 600 μM and stored at −18° C. Further dilution steps in Dulbecco's minimal essential medium (MEM) are carried out for the test. In each case, 100 μl of the individual test substance dilutions are added together with 100 μl of serum-free Dulbecco's MEM (-FCS) to the rinsed cells.

After incubating at 37° C. and at 5% $CO_2$ for 3 h, the cells are infected with herpes simplex virus type I (ATCC VR733, HSV 1 F strain) at concentrations at which the cell lawn is completely destroyed within the space of 3 days. In the case of HSV 1, the size of the infection is 500 plaque-forming units (PFU) per well, and in the case of HSV 2, 350 PFU/well. The experimental mixtures then contain test substances at concentrations of from 80 μM to 0.04 μM in MEM, supplemented with 100 U/ml penicillin G and 100 mg/l streptomycin. All the experiments are carried out as duplicate determinations with the exception of the controls, which are carried out eight times for each plate.

The experimental mixtures are incubated at 37° C. and at 5% $CO_2$ for 17 h. The cytotoxicity of the test substances is determined after a total incubation period of 20 h by microscopic assessment of the cell cultures. The highest concentration of a preparation which still fails to elicit any microscopically recognizable cell damage under the stated experimental conditions is designated the maximum tolerated dose (MTD).

There then follows the addition of FCS to a final concentration of 4% with further incubation at 37° C. and at 5% $CO_2$ for 55 h. The untreated infection controls then show a complete cytopathic effect (CPE). After having been assessed microscopically, the cell cultures are then stained with neutral red in accordance with the vital staining method of Finter (1966). The antiviral activity of a test substance is defined as the minimum inhibitory concentration (MIC) which is required in order to protect 30–60% of the cells from the cytopathogenic effect occasioned by the virus.

The results of the experiments are presented in Tables 1–6.

Table 1:

Antisense oligonucleotides complementary to the translation start of the IE 110 gene of HSV 1, and their antiviral activity. The phosphodiester bonds replaced by a phosphorothioate bridge were indicated in the sequence by *.

| | | | |
|---|---|---|---|
| AO12 | G*C*T C C A T G G G G T C G T A T *G*C | 80.0 μM | (SEQ ID NO: 19) |
| AO11 | G*G*G C T C C A T G G G G T C G T*A*T | 80.0 μM | (SEQ ID NO: 18) |
| AO5 | G*G*G G C T C C A T G G G G T C G*T*A | 26.7 μM | (SEQ ID NO: 12) |
| AO10 | C*G*G G G C T C C A T G G G G T C*G*T | 80.0 μM | (SEQ ID NO: 17) |
| AO1 | G*C*G G G G C T C C A T G G G G T*C*G | 2.9 μM | (SEQ ID NO: 8) |
| AO4 | G*G*C G G G G C T C C A T G G G G*T*C | 26.7 μM | (SEQ ID NO: 11) |
| AO8 | G*G*G C G G G G C T C C A T G G G G*T | 80.0 μM | (SEQ ID NO: 15) |
| AO3 | G*G*G G C G G G G C T C C A T G G*G*G | 8.9 μM | (SEQ ID NO: 10) |
| AO9 | C*C*G G G G C G G G G C T C C A T G*G*G | >80.0 μM | (SEQ ID NO: 16) |
| AO38: | 5'-FAM-G C G G G G C T C C A T G G G G T*C*G-3' | 4.5 | (SEQ ID NO: 39) |
| AO39: | 5'-G*C*G G G G C T C C A T G G G G G T*C*G-P-3' | 27 | (SEQ ID NO: 40) |
| AO40: | 5'-G*C*G G G G C T C C A T G G G G T*C*G-P-DMAB-3' | 27 | (SEQ ID NO: 41) |
| AO41: | 5'-G-FAM-G C G G G G C T C C A T G G G G T*C*G-P-VITE-3' | 3 | (SEQ ID NO: 42) |
| AO42: | 5'-G*G*C*G G G G C T C C A T G G G G G*T*C-3' | 9 | (SEQ ID NO: 43) |
| AO43: | 5'-G*G*C*G G G G C T C C A T G G G G G*T*C-P-$C_{14}$-3' | 3 | (SEQ ID NO: 44) |
| AO44: | 5'-G*G*C*G G G G C T C C A T G G G G G*T*C-P-BAT-3' | 1 | (SEQ ID NO: 45) |
| | 3'...G G C C C C G C C C C G A G G T A C C C C C A G C A T A C G...5' | | (SEQ ID NO: 49) |
| | IE110 mRNA | | |

Table 2:

Antisense oligonucleotides complementary to the UL30 gene of HSV 1, and their antiviral activity. The phosphodiester bonds replaced by a phosphorothioate bridge were indicated in the sequence by *.

| | | MIC | |
|---|---|---|---|
| AO2: | 5'-G*C*A G G A G G A T G C T G A G G A*G*G-3' | 26 μM | (SEQ ID NO: 9) |
| AO13: | 5'-C*C*G G A A A A C A T C G C G G T T*G*T-3' | >80 μM | (SEQ ID NO: 20) |
| AO14: | 5'-C*C*G G G G G C G C T T G G C C G G*G*G-3' | >80 μM | (SEQ ID NO: 21) |

-continued

|       |                                                          | MIC    |                |
|-------|----------------------------------------------------------|--------|----------------|
| AO15: | 5'-C*A*G C A G C T T G C G G G G C T T*G*G-3'            | >80 μM | (SEQ ID NO: 22) |
| AO16: | 5'-C*C*C C C A A C A G G T G G G A G A*A*G-3'            | >80 μM | (SEQ ID NO: 23) |
| AO17: | 5'-G*G*G G G G T G C C A C A C T T C G*G*G-3'            | >80 μM | (SEQ ID NO: 24) |
| AO18: | 5'-C*C*C A C C C G A A C C C C T A A A*G*A-3'            | >80 μM | (SEQ ID NO: 25) |
| AO27: | 5'-G*C*A G G A G G A T G C T G A G G A*G*G-P-$C_{14}$-3' | 27     | (SEQ ID NO: 34) |
| AO28: | 5'-G*C*A G G A G G A T G C T G A G G*A*G*G-P-$C_{12}$-3' | 80     | (SEQ ID NO: 35) |
| AO29: | 5'-G*C*A G G A G G A T G C T G A G G*A*G*G-P-$C_{14}$-3' | 27     | (SEQ ID NO: 36) |
| AO30: | 5'-G*C*A G G A G G A T G C T G A G G*A*G*G-P-$C_{16}$-3' | 9      | (SEQ ID NO: 37) |
| AO31: | 5'-G*C*A G G A G G A T G C T G A G G*A*G*G-P-$C_{18}$-3' | 3      | (SEQ ID NO: 38) |

Table 3:

Antisense oligonucleotides complementary to the UL48 gene of HSV 1, and their antiviral activity. The phosphodiester bonds replaced by a phosphorothioate bridge were indicated in the sequence by *.

|       |                                                  | MIC    |                |
|-------|--------------------------------------------------|--------|----------------|
| AO6:  | 5'-A*A*G A G G T C C A T T G G G T G G*G*G-3'    | 26 μM  | (SEQ ID NO: 13) |
| AO19: | 5'-G*T*C C G C G T T C A T G T C G G C*A*A-3'    | >80 μM | (SEQ ID NO: 26) |
| AO20: | 5'-A*A*C A G A G G C A G T C A A A C A*G*G-3'    | >80 μM | (SEQ ID NO: 27) |
| AO21: | 5'-A*T*A C G G G A A A G A C G A T A T*C*G-3'    | >80 μM | (SEQ ID NO: 28) |

Table 4:

Antisense oligonucleotides complementary to the UL52 gene of HSV 1, and their antiviral activity. The phosphodiester bonds replaced by a phosphorothioate bridge were indicated in the sequence by *.

|       |                                                  | MIC    |                |
|-------|--------------------------------------------------|--------|----------------|
| AO7:  | 5'-G*G*C C C T G C T G T T C C G T G G*C*G-3'    | 26 μM  | (SEQ ID NO: 14) |
| AO22: | 5'-G*T*C T T C C T G C C C C A T T G C*G*T-3'    | >80 μM | (SEQ ID NO: 29) |
| AO23: | 5'-T*G*C G T C C G C G C G C C C A A G*G*G-3'    | >80 μM | (SEQ ID NO: 30) |

Table 5:

|       |                                                  | MIC   |                |
|-------|--------------------------------------------------|-------|----------------|
| AO1:  | 5'-G*C*G G G G C T C C A T G G G G G T*C*G-3'    | 8 μM  | (SEQ ID NO: 8) |
| AO24: | 5'-G C G G G G C T C C A T G G G G G*T*C*G-3'    | 27 μM | (SEQ ID NO: 31) |
| AO25: | 5'-G*C*G*G G C T C C A T G G G G G T C G-3'      | 27 μM | (SEQ ID NO: 32) |
| AO26: | 5'-PY-G*C*G G G G C T C C A T G G G G G T*C*G-3' | 8 μM  | (SEQ ID NO: 33) |

Table 6: Controls

|       |                                                            | MIC |                |
|-------|------------------------------------------------------------|-----|----------------|
| AO32: | 5'-C*C*A G G G T A C A G G T G G C C G G*C*C-3'            | >80 | (SEQ ID NO: 46) |
| AO33: | 5'-C*C*A G G G T A C A G G T G G C C G G*C*C-p-$C_{14}$-3' | >80 | (SEQ ID NO: 47) |
| AO34: | 5'-C*C*A G G G T A C A G G T G G C C G*C*C-p-$C_{12}$-3'   | >80 | (SEQ ID NO: 48) |
| AO35: | 5'-C*C*A G G G T A C A G G T G G C C G G*C*C-p-$C_{14}$-3' | >80 | (SEQ ID NO: 47) |

EXAMPLE 3

Investigation of the in-vivo antiviral activity of test substances against herpesviruses NMRI mice (NMRI: Naval Medical Research Institute), specific pathogen free, approximately 15 g in weight, were infected intraperitoneally with herpes simplex type 1 and subsequently treated intraperitoneally, subcutaneously or per os with the compounds described below. The dosage of the compounds according to the invention was between 1 and 100 μg. The animals were treated twice a day for 2.5 days, beginning after the infection. Comparison of the course of the disease and the survival rate in the treated animals with those in the untreated infection controls was used to determine the success of the treatment. In place of the compounds to be tested, the untreated infection controls were administered a water-soluble methylhydroxyethyl cellulose (viscosity 300 Pa in 2% solution) ((R) Tylose MH 300 P).

The following oligonucleotide was tested:

5'-G*C*G G G G C T C C A T G G G G G T*C*G-3' (SEQ ID NO: 50)

A preliminary assessment indicated that the oligonucleotide examined was active as compared with the controls in the concentration range which was tested.

---

We claim:

1. An antisense oligonucleotide having the sequence

AO1 (Herp099):

5'-GCGGGGCTCCATGGGGGTCG-3' (SEQ ID NO:1)

AO2 (Herp018):

5'-GCAGGAGGATGCTGAGGAGG-3' (SEQ ID NO:2)

AO4 (Herp112):

5'-GGCGGGGCTCCATGGGGGTC-3' (SEQ ID NO:4)

AO5 (Herp034):

5'-GGGGCTCCATGGGGGTCGTA-3' (SEQ ID NO:5)

AO6 (Herp024):

5'-AAGAGGTCCATTGGGTGGGG-3' (SEQ ID NO:6)

or

AO7 (Herp028):

5'-GGCCCTGCTGTTCCGTGGCG-3' (SEQ ID NO: 7)

2. An antisense oligonucleotide as claimed in claim 1, wherein one or more, but not all, nucleotides are connected by phosphorothioate bridges, (SEQ ID NOS:8–14) phosphorodithioate bridges or methylphosphonate bridges.

3. An antisense oligonucleotide as claimed in claim 2, wherein, independently of each other at the respective ends, the first two to four nucleotides are connected by phosphorothioate bridges or phosphorodithioate bridges.

4. An antisense oligonucleotide as claimed in claim 1, which oligonucleotide is linked to 3'-phosphate, fluorescein, lipophilic molecules, steroids, polyethylene glycol, oligoethylene glycol, vitamin E, intercalating agents, ($C_1$–$C_{18}$)-alkyl phosphate diesters, optionally substituted once or more than once by Cl, Br and/or OH, or to —O—$CH_2$–CH(OH)—O—($C_{12}$–$C_{16}$)-alkyl.

5. An antisense oligonucleotide as claimed in claim 4, which oligonucleotide is linked to ($C_{12}$–$C_{20}$)-alkyl, cholesterol, testosterone, hexaethylene glycol or pyrene.

6. A process for preparing the antisense oligonucleotides as claimed in claim 1, wherein the oligonucleotides are synthesized chemically.

* * * * *